(12) United States Patent
Kawashima et al.

(10) Patent No.: US 7,847,113 B2
(45) Date of Patent: Dec. 7, 2010

(54) PHOSPHOLIPIDS INCLUDING LONG-CHAIN POLYUNSATURATED FATTY ACIDS AS CONSTITUENTS, AND USE OF SUCH PHOSPHOLIPIDS

(75) Inventors: Hiroshi Kawashima, Takatsuki (JP); Motoo Sumida, Uji (JP); Akiko Shiraishi, Ibaraki (JP)

(73) Assignee: Suntory Holdings Limited, Osaka-shi, Osaka (JP)

( * ) Notice: Subject to any disclaimer, the term of this patent is extended or adjusted under 35 U.S.C. 154(b) by 845 days.

(21) Appl. No.: 10/591,329

(22) PCT Filed: Feb. 28, 2005

(86) PCT No.: PCT/JP2005/003344

§ 371 (c)(1),
(2), (4) Date: Jun. 14, 2007

(87) PCT Pub. No.: WO2005/083101

PCT Pub. Date: Sep. 9, 2005

(65) Prior Publication Data

US 2008/0020124 A1    Jan. 24, 2008

(30) Foreign Application Priority Data

Mar. 1, 2004 (JP) .............................. 2004-056928

(51) Int. Cl.
*C07F 9/02* (2006.01)
(52) U.S. Cl. .............................. 554/79; 554/78; 554/80; 426/648; 426/662
(58) Field of Classification Search .................... 554/78, 554/79, 80; 426/648, 662
See application file for complete search history.

(56) References Cited

FOREIGN PATENT DOCUMENTS

| | | |
|---|---|---|
| JP | 8-59678 | 3/1996 |
| JP | 11-35587 | 2/1999 |
| JP | 2000-245492 | * 9/2000 |
| JP | 2003-048831 | * 2/2003 |

OTHER PUBLICATIONS

K. Imaizumi, "Digestive Absorption and Physiological Activity of Phospholipids." *Clinical Nutrition (Rinsho Eiyo)*, 1985, vol. 67, p. 119. [partial translation].
K. Yazawa et al. "Production of Icosapentaenoic Acid From Marine Bacteria and Its Genetic Engineering." *Oil Chemistry (Abura Kagaku)*, 1995, vol. 44, pp. 87-93. [English Abstract & partial translation].
S. Shobou, "Oils and Fats Handbook." 1988, p. 184. [partial translation].
G. Toffano et al., "Pharmacological Effects of Phosphatidylserine Liposomes." *Nature*, 1976, vol. 260, pp. 331-333.
G. Toffano et al., "Pharmacokinetics of Radiolabelled Brain Phosphatidylserine." *Clinical Trials Journal*, 1987, vol. 24, No. 1, pp. 18-24.
S. Jareonkitmongkol et al., "A Novel Δ5-Desaturase-Defective Mutant of *Mortierella alpina* 1S-4 and Its Dihomo-γ-Linolenic Acid Productivity." *Applied and Environmental Microbiology*, 1993, vol. 59, No. 12, pp. 4300-4304.
International Search Report dated Jun. 14, 2005 issued in International PCT Application No. PCT/JP2005/003344 [in Japanese].

* cited by examiner

*Primary Examiner*—Deborah D Carr
(74) *Attorney, Agent, or Firm*—Drinker Biddle & Reath LLP

(57) ABSTRACT

The present invention provides a method of efficiently and stably producing LCPUFA-PL. Specifically, the invention provides a method for producing phospholipids that contain LCPUFA as a constituent (LCPUFA-PL), wherein lipid producing cells producing lipids that contain long-chain polyunsaturated fatty acids (LCPUFA) are used as a starting material, the method including a PL extracting step of extracting phospholipids (PL) from defatted cells obtained by extracting triglyceride (TG)-containing oil or fat from the lipid producing cells.

9 Claims, No Drawings

PHOSPHOLIPIDS INCLUDING LONG-CHAIN POLYUNSATURATED FATTY ACIDS AS CONSTITUENTS, AND USE OF SUCH PHOSPHOLIPIDS

CROSS REFERENCE TO RELATED APPLICATIONS

This application is a National Stage of International Application No. PCT/JP2005/003344, filed Feb. 28, 2005, and which claims benefit of Japanese patent application no. 2004-056928, filed on Mar. 1, 2004, and are incorporated by reference herein in their entirety.

TECHNICAL FIELD

The present invention relates to a producing method of phospholipids including long-chain polyunsaturated fatty acids as constituents, and use of such phospholipids. The invention particularly relates to a method for efficiently and stably producing phospholipids, and to phospholipids produced by the method, and representative use of such phospholipids.

BACKGROUND ART

Phospholipids (PL) are known to possess various physiological functions, including brain function improving effect, anti-stress effect, and cholesterol reducing action. PL occur in various forms, well-known examples of which include phosphatidylcholine (PC), phosphatidylserine (PS), phosphatidylethanolamine (PE), and phosphatidylinositol (PI). These different forms of PL have different functions and properties.

Among these different types of PL, phospholipids whose constituents are long-chain polyunsaturated fatty acids (may be referred to as "LCPUFA" hereinafter) with 20 or greater carbon atoms (may be referred to as "LCPUFA-PL" for convenience of explanation) are known to exhibit superior brain function improving effect, as compared with phospholipids whose constituents are not LCPUFA (may be referred to as "non-LCPUFA-PL" for convenience of explanation) (see Non-Patent Publication 1, for example). Specific examples of LCPUFA include, for example, docosahexaenoic acid (DHA), arachidonic acid (AA) and the like.

Non-phospholipid LCPUFA derivatives are also known to possess brain function improving effects (see Patent Publication 1, for example). However, unlike phospholipids such as the LCPUFA-PL or Non-LCPUFA-PL, the non-phospholipid LCPUFA derivatives are believed to act on the hippocampus of the cerebrum to improve the brain functions.

The LCPUFA-PL is considered to provide superior brain function improving effect because (1) it has the structure actually present in the brain, (2) it can pass through the blood brain barrier, and (3) it can reach the brain tissue or other tissues in the body without being captured or modified in the liver, since the molecule is absorbed without entering the liver.

The following more specifically describes these reasons. (1) The LCPUFA in the brain is known to exist almost entirely in the form of phospholipids. More specifically, most of LCPUFA exist as compounds such as PC, PS, PE, and PI, and therefore exhibit a variety of functions in the brain. (2) The phospholipids can reach the brain tissue. This has been proved by an experiment in which orally administered labeled-phospholipids were detected in the brain tissue (see Non-Patent Publication 2). (3) When absorbed, one of the two fatty acid molecules of the phospholipids is hydrolyzed to generate lysophospholipids in the digestive system. The lysophospholipids are absorbed in the small intestine and reassembled into phospholipids in the small intestine cells before they are absorbed through the lymph vessels (Non-Patent Publication 3). In this manner, the LCPUFA-PL circulates through the body without entering the liver.

Conventionally, the LCPUFA-PL has been produced by being prepared or purified from organs, eggs, or other parts of animals containing a large amount of LCPUFC-PL. In one specific example, the LCPUFA-PL is prepared from the cow brain, or a phospholipid fraction from the pig liver or fish egg is purified (see Patent Publications 2 and 3). Further, particular species of marine bacteria are known to produce LCPUFA-PL (see Non-Patent Publication 4). Furthermore, it is also known that arachidonic acid-producing filamentous bacteria produce a small amount of phospholipids containing arachidonic acid in addition to a large amount of triglycerides containing arachidonic acid (see Non-Patent Publication 5).

In the industrial production of phospholipids, phospholipids are generally extracted together with oil or fat, when the oil or fat, of which primary ingredient are triglycerides, is extracted from a starting material. Hexane or the like solvent is used as a solvent for extraction.

The extracted oil or fat includes gum substance, which may cause the coloring and foaming of the oil or fat. Therefore the gum substance is removed through a gum-removing process, in which almost all parts of phospholipids are transferred to the gum substance. Accordingly, phospholipids are produced by purification of the gum substance.

In the case where soy bean lecithin is produced as phospholipids, raw oil is extracted from soy, which is a starting material in this case, by using hexane as a solvent. The residual defatted soy is used as food, feedstuff or the like. As the raw oil, on the other hand, includes gum substance, the gum substance is separated through a gum-removing process and then purified. Through the process the soy bean lecithin is produced. When the content of the soy bean lecithin or phospholipids is detected after the aforementioned series of production steps of the soy bean lecithin, from 1.5% to 2.5% of phospholipids is contained in the raw oil indeed, but the content of phospholipids in the purified oil is no more than 0.05%. Consequently, it becomes apparent that the phospholipids are removed mainly through gum-removing process (see Non-Patent Publication 6).

[Patent Publication 1]
Japanese Laid-Open Patent Publication No. 48831/2003 (Tokukai 2003-48831) (published on Feb. 21, 2003)
[Patent Publication 2]
Japanese Laid-Open Patent Publication No. 35587/1999 (Tokukaihei 11-35587) (Published on Feb. 9, 1999)
[Patent Publication 3]
Japanese Laid-Open Patent Publication No. 59678/1996 (Tokukaihei 08-59678) (Published on Mar. 5, 1996)
[Non-Patent Publication 1]
G. Toffano et al., Nature Vol. 260 p 331-333 (1976)
[Non-Patent Publication 2]
G. Toffano et al. Clinical Trial Journal Vol. 24 p 18-24 (1987)
[Non-Patent Publication 3]
Katsumi Imaizumi, Clinical Nutrition (Rinsho Eiyo), Vol. 67, p. 119 (1985)
[Non-Patent Publication 4]
Kazunaga Yazawa et al., Oil Science (Abura Kagaku), Vol. 44, pp. 787-793 (1995)
[Non-Patent Publication 5]
S. jareonkitmongkol et al., Apple Environ Microbiol Vol. 59 p 4300-4304 (1993)

[Non-Patent Publication 6]

Oils and Fats Handbook, Saiwai Shobou, p. 178-184 (1988)

But through the conventional techniques, it is difficult to produce LCPUFA-PL efficiently and stably.

Specifically, sources of LCPUFA-PL are limited and only a small amount of LCPUFA-PL can be obtained because the LCPUFA-PL currently available all derive from the aforementioned animal organs, or the egg yolk of animals. The supply is therefore unstable, and the same quality cannot always be obtained. Further, with the epidemic of the mad-cow disease, it has become very difficult to use the cow brain or other animal organs.

As for the technique using microbe, in the LCPUFA-PL derived from marine bacteria, the majority of its fatty acids are branched fatty acids which are distinct to bacteria and are rarely seen in humans or other animals. The LCPUFC-PL derived from marine bacteria is therefore not suitable as a nutritional composition for human consumption. Further, though arachidonic acid-producing filamentous bacteria produce phospholipids containing arachidonic acid, only a small amount is detected in a mixture of a large amount of triglycerides. Therefore it is difficult to apply this method in an industrial application.

The present invention was made in view of the foregoing problems. An object of the invention is to provide a technique to produce LCPUFA-PL efficiently and stably, and to provide low-cost LCPUFA-PL with a stable quality in stable quantity. Another object of the invention is to provide representative application of the technique.

DISCLOSURE OF INVENTION

The inventors of the present invention diligently worked to solve the foregoing problems. In accomplishing the present invention, the following findings (1) and (2) were obtained when lipid producing cells that produce LCPUFA lipids were used as a starting material to produce LCPUFA-PL. (1) In extracting triglycerides from cells, the fraction of the extract containing triglycerides as a major component contained hardly any phospholipids, contrary to an expected outcome of finding phospholipids with the triglycerides. In the residual cells obtained by the extraction of the triglycerides, a large amount of LCPUFA-PL remained. (2) From the defatted cells, it was possible to easily extract LCPUFA-PL with a simple procedure using an extractant such as an organic solvent.

That is, the present invention provides a method for producing phospholipids that contain LCPUFA as a constituent (LCPUFA-PL), wherein lipid producing cells producing lipids that contain long-chain polyunsaturated fatty acids (LCPUFA) are used as a starting material, the method including a PL extracting step of extracting phospholipids (PL) from defatted cells obtained by extracting triglyceride (TG)-containing oil or fat from the lipid producing cells.

It is preferable that the producing method further include an oil or fat extracting step of extracting TG-containing oil or fat from the lipid producing cells and obtaining the defatted cells, the oil or fat extracting step being carried out before the PL extracting step.

The lipid producing cells used in the invention are not particularly limited, but are preferably at least one kind selected from the group consisting of: *Mortierella; Conidiobolus; Pythium; Phytophthora; Penicillium; Cladosporium; Mucor; Fusarium; Aspergillus; Rhodotorula; Entomophthora; Echinosporangium*; and *Saprolegnia*. It is preferable that the lipid producing cells that belong to genus *Mortierella* also belong as subgenus *Mortierella*, and that the cells that belong to subgenus *Mortierella* are *Mortierella alpina*.

It is preferable in the producing method that, in the PL extracting step, an extract of at least one of an aliphatic organic solvent and water, or supercritical carbon dioxide gas be used as an extractant used to extract PL from the defatted cells. The aliphatic organic solvent is preferably a saturated hydrocarbon, an alcohol, a mixed solvent of saturated hydrocarbon and alcohol, or a mixed solvent of halogenated hydrocarbon and alcohol. It is preferable that the extract be at least one of hexane, ethanol, methanol, hydrous ethanol, isopropyl alcohol, and acetone, and that the extract be a mixed solvent of hexane and ethanol. A hexane:ethanol ratio of the mixed solvent of hexane and ethanol is preferably in a range of 4:1 to 0:6 by volume.

It is preferable in the producing method that, in the oil or fat extracting step, the oil or fat be extracted from the lipid producing cells using at least one of compression extraction employing applied pressure, rendering extraction, and extraction using an extractant. It is preferable that an extract of at least one of an aliphatic organic solvent and water, or supercritical carbon dioxide gas be used as the extractant used to extract PL from the defatted cells. Hexane is preferably used as the aliphatic organic solvent. Preferably, the lipid producing cells used in the oil or fat extracting step are dried cells.

Phospholipids according to the present invention are produced by the foregoing producing method, and include LCPUFA as a constituent. The constituent LCPUFA is not particularly limited, but is preferably at least one kind selected from the group consisting of: eicosadienoic acid, eicosatrienoic acid, eicosatetraenoic acid, eicosapentaenoic acid, docosadienoic acid, docosatrienoic acid, docosatetraenoic acid, docosapentaenoic acid, docosahexaenoic acid, tetracosadienoic acid, tetracosatrienoic acid, tetracosatetraenoic acid, tetracosapentaenoic acid, and tetracosahexaenoic acid.

At least one of C—C double bonds in a LCPUFA molecule may be conjugated, and the LCPUFA preferably includes arachidonic acid and/or docosahexaenoic acid. It is preferable that a proportion of arachidonic acid with respect to total fatty acids contained as constituents of total LCPUFA-PL is 0.3 percent by weight or greater.

Specifically, the LCPUFA-PL is preferably at least one kind of glycerophospholipid selected from the group consisting of: phosphatidylcholine; phosphatidylserine; phosphatidylethanolamine; phosphatidylinositol; phosphatidic acid; and cardiolipin. In the case where the LCPUFA-PL is at least phosphatidylcholine, it is preferable that a proportion of arachidonic acid with respect to total fatty acids contained as constituents of total phosphatidylcholine be 15 percent by weight or greater. In the case where the LCPUFA-PL is at least phosphatidylserine, it is preferable that a proportion of arachidonic acid with respect to total fatty acids contained as constituents of total phosphatidylserine be 5 percent by weight or greater.

In Phospholipids according to the present invention, the LCPUFA-PL includes at least phosphatidylcholine and phosphatidylserine, and the LCPUFA includes at least arachidonic acid, and a proportion of arachidonic acid with respect to total fatty acids contained as constituents of total phosphatidylcholine is 40 percent by weight or greater, and a proportion of arachidonic acid with respect to total fatty acids contained as constituents of total phosphatidylserine is 20 percent by weight or greater.

The phospholipids may be adapted so that the LCPUFA-PL includes phosphatidylcholine that at least includes dihomo-γ-linolenic acid as LCPUFA, and that a proportion of dihomo-γ-linolenic acid with respect to total fatty acids contained as constituents of total phosphatidylcholine is 3 percent by weight or greater. Further, the phospholipids may be adapted so that the LCPUFA-PL includes phosphatidylserine that at least includes dihomo-γ-linolenic acid as LCPUFA, and that a proportion of dihomo-γ-linolenic acid with respect to total fatty acids contained as constituents of total phosphatidylserine is 1 percent by weight or greater.

A method of producing a lipid composition according to the present invention includes: a PL extracting step of the foregoing producing method; and a solution preparing step of preparing a phospholipid solution by dissolving the LCPUFA-PL-containing PL obtained in the PL extracting step in a liquid lipid that contain LCPUFA as a constituent.

It is preferable that the producing method further include an oil or fat extracting step, wherein oil or fat obtained in the oil or fat extracting step is used as the liquid lipid, and that an amount of oil or fat extracted in the oil or fat extracting step be suppressed, so as to extract in the PL extracting step the LCPUFA-PL as a lipid composition dissolved in the liquid lipid.

A lipid composition according to the present invention is produced by the method of producing a lipid composition, and at least includes: LCPUFA-PL; and a liquid lipid including LCPUFA as a constituent. It is preferable in the lipid composition that a proportion of LCPUFA with respect to total fatty acids of the liquid lipid be 11 percent by weight or greater.

A lipid composition according to the present invention is not necessarily required to be obtained by the method of producing a lipid composition as long as it contains the phospholipids.

A lipid composition according to the present invention may be used as a nutritional composition, and may be processed into a capsule or tablet, for example.

In the present invention, the lipid composition may be used in food. That is, the present invention includes food that contains the lipid composition. Further, in the present invention, food may include an oil-in-water dispersion liquid in the form of a liposome formed by the phospholipids. A specific example of food is a nutriment.

For a fuller understanding of the nature and advantages of the invention, reference should be made to the ensuing detailed description.

BEST MODE FOR CARRYING OUT THE INVENTION

The following will describe one embodiment of the present invention in detail. It should be noted that the invention is not limited in any way by the following descriptions. Specifically, the present embodiment describes phospholipids and a producing method thereof, lipid composition and a producing method thereof, and use of the invention, in order of appearance.

(I) Phospholipids According to the Invention, and a Producing Method Thereof

The present invention provides phospholipids that include LCPUFA as constituents (LCPUFA-PL), using, as a starting material, lipid producing cells that produce lipids whose constituents are LCPUFA. The invention also provides a producing method of phospholipids (referred to simply as a "producing method" where appropriate), in which LCPUFA-PL is produced. Specifically, a producing method according to the present invention at least includes a PL extracting step of extracting phospholipids (PL) from defatted cells obtained by extracting triglyceride (TG)-containing oil or fat from lipid producing cells.

That is, in the present invention, the defatted cells (residual cells) from which an oil or fat such as triglycerides has been removed are used as a source of LCPUFA-PL. As such, the invention may include an oil or fat extracting step, carried out before the PL extracting step, of extracting a TG-containing oil or fat from the lipid producing cells and obtaining defatted cells.

<Lipid Producing Cells>

The lipid producing cells used as a starting material in the present invention are not particularly limited as long as they are microorganisms capable of producing LCPUFA-PL. Specific examples include *Mortierella, Conidiobolus, Pythium, Phytophthora, Penicillium, Cladosporium, Mucor, Fusarium, Aspergillus, Rhodotorula, Entomophthora, Echinosporangium*, and *Saprolegnia*.

Lipid producing cells used as a starting material are selected according to the type of LCPUFA produced. For example, only one kind of strain may be used, or two or more combinations of strains may be used.

Among these lipid producing cells, many species or strains of *Mortierella* are known to be capable of producing LCPUFA-PL that includes arachidonic acid (AA) as a constituent of LCPUFA (hereinafter AA-PL). When *Mortierella* are used, it is preferable that the cells belong to subgenus *Mortierella*, examples of which include *Mortierella alpina, Mortierella polycephala, Mortierella exigua, Mortierella hygrophila*, and *Mortierella elongata*.

More specifically, bacterial strains of subgenus *Mortierella* capable of producing AA-PL are, for example, *M. polycephala* IFO6335, *M. elongata* IFO8570, *M. exigua* IFO8571, *M. hygrophila* IFO5941, *M. alpina* IFO8568, ATCC16266, ATCC32221, ATCC42430, CBS219.35, CBS224.37, CBS250.53, CBS343.66, CBS527.72, CBS529.72, CBS608.70, and CBS754.68.

Other than subgenus *Mortierella*, the following strains are capable of producing AA-PL: *Echinosporangium transversalis* ATCC16960, *Conidiobolus heterosporus* CBS138.57, and *Saprolegnia lapponica* CBS284.38.

All of these strains are available from Institute for Fermentation, Osaka (IFO), American Type Culture Collection, ATCC, and Centrralbureau voor Schimmelcultures (CBS), among others.

As another example of a strain of subgenus *Mortierella* capable of producing AA-PL, the strain *M. elongata* SAM0219 (International Deposit No. FERMBP-1239 based on Budapest Treaty), separated from soil by a research group including the inventors of the present invention, is available.

Further, a more specific example of microorganisms that belong to subgenus *Mortierella* and is capable of producing LCPUFA-PL (DGLA-PL) whose LCPUFA constituent is dihomo-γ-linolenic acid (DGLA) is the strain *M. elongata* SAM 1860 (International Deposit No. FERMBP-3589 based on Budapest Treaty) separated from soil by a research group including the inventors of the present invention.

Further, a more specific example of microorganisms that belong to subgenus *Mortierella* and is capable of producing LCPUFA-PL (mead acid-PL) whose LCPUFA constituent is mead acid is the strain *M. alpina* SAM2086 (International Deposit No. FERMBP-6032 based on Budapest Treaty) separated from soil by a research group including the inventors of the present invention.

<Culturing of Lipid Producing Cells>

The present invention is adapted to culture microorganisms (lipid producing cells) capable of producing LCPUFA-PL, so as to produce the cells in a sufficient amount. As such, a producing method according to the present invention may include a lipid producing cells culturing step of culturing lipid producing cells.

A method of culturing the lipid producing cells is not specifically limited, and a conventional method can be used depending on the type of lipid producing cells. Generally, a liquid medium or solid medium is inoculated with the spores or mycelia of lipid producing cells to be cultured, or with a pre-culture solution of the lipid producing cells. When the cells are required in a large quantity, use of a liquid medium is often more preferable. The culturing equipment is not particularly limited. For a small culture, the cells may be cultured by shaking cultivation in a liquid medium placed in various types of test tubes or flasks, or by static cultivation by inoculating an agar plate. For a large culture, various types of fermentors, including a jar fermentor can be used.

The type of culture medium used is not particularly limited either, and is suitably selected and prepared from known components according to the type of lipid producing cells used. Alternatively, a medium of a known composition, or a commercially available medium can be used.

When a liquid medium is used, the carbon source is not particularly limited and common sugars can be suitably used. Specific examples of such sugars include glucose, fructose, xylose, saccharose, maltose, soluble starch, syrup, glycerol, and mannitol. These carbon sources can be used either alone or in a combination of two or more kinds.

The nitrogen source is not particularly limited either, and conventional sources can be suitably used. Some of the examples include: natural sources such as peptone, yeast extract, malt extract, meat extract, cazamino acid, corn steep liquor, soybean protein, defatted soybean, and cotton seed lees; organic sources such as urea; and inorganic sources such as sodium nitrate, ammonium nitrate, and ammonium sulfate. Among these examples, natural sources derived from soy beans are particularly suitable in the present invention, though the type of suitable source varies depending on the type of cultured strain.

Specific examples of such sources include soy beans, defatted soy beans, soy bean flakes, edible soy bean proteins, bean-curd refuse, soya milk, and soy flour. Among these examples, heat-denatured defatted soy beans, or more preferably defatted soy beans obtained by a heat treatment of about 70° C. to 90° C. and subsequent removal of an ethanol-soluble component can be used. These nitrogen sources can be used either alone or in a combination of two or more kinds.

Components other than the carbon source or nitrogen source are not particularly limited either. As required, a known mineral nutrient source can be suitably selected and added. Examples of such nutrient sources include: ions of inorganic acid such as ions of phosphoric acid; ions of alkali metals or alkali earth metals, such as calcium ion, sodium ion, magnesium ion, and calcium ion; metal ions of groups VIIB to VIII, such as iron, nickel, cobalt, and manganese; metal ions of groups IB to IIB, such as copper and zinc; and various vitamins.

The content (percent addition) of each component in a liquid medium is not particularly limited, and a conventional amount can be suitably adopted as long as it does not inhibit the growth of the lipid producing cells. In actual practice, the total amount of carbon source added is preferably in a range of generally from 0.1 percent by weight to 40 percent by weight, or more preferably 1 percent by weight to 25 percent by weight. In the case of a nitrogen source, the total amount added is preferably in a range of generally from 0.01 percent by weight to 10 percent by weight, or more preferably 0.1 percent by weight to 10 percent by weight. In the case of a feeding culture, it is preferable that the initial amount of carbon source added be in a range of 1 percent by weight to 5 percent by weight, and that the initial amount of nitrogen source added be in a range of 0.1 percent by weight to 6 percent by weight. Both the carbon source and nitrogen source can be fed to the culture medium; however, it is more preferable to feed only the carbon source.

Note that, in a producing method according to the present invention, precursors of unsaturated fatty acids can be added to the medium in order to increase the yield of LCPUFA-containing unsaturated fatty acids. Non-limiting examples of the precursors of unsaturated fatty acids include: hydrocarbons such as hexadecane or octadecane; fatty acids or salts thereof, such as oleic acid or linoleic acid; fatty acid esters, such as ethylester, glycerine fatty acid ester, or sorbitan fatty acid ester; and oils or fats, such as olive oil, soy bean oil, rapeseed oil, cotton oil, and coconut oil. These precursors may be used either alone or in a combination of two or more kinds.

The amount of precursors of unsaturated fatty acids added is not particularly limited. Generally, the precursors of unsaturated fatty acids are added in a range of 0.001 percent to 10 percent with respect to the total weight of the medium, or more preferably 0.5 percent to 10 percent with respect to the total weight of the medium. The lipid producing cells may be cultured using these precursors as a sole carbon source.

The culture conditions are not particularly limited, and are suitably selected according to the type of cultured strain. For example, the culture temperature is generally in a range of 5° C. to 40° C., or more preferably 20° C. to 30° C. Alternatively, the cells may be grown first in a temperature range of 20° C. to 30° C., and then 5° C. to 20° C. With such temperature control whereby cells are cultured first in a relatively high temperature range and then in a lower temperature range, the proportion of polyunsaturated fatty acids (PUFA) in the resulting unsaturated fatty acids can be increased.

The pH of the medium is not particularly limited either. Generally, a pH range of 4 to 10 is used, or more preferably a pH range of 5 to 9 is used. The cultivation period is not particularly limited either. Generally, the cultivation period is 2 to 30 days, preferably 5 to 20 days, and more preferably 5 to 15 days. The external process carried out on the medium is not particularly limited, and is suitably selected from conventional cultivation methods, including stirring aeration cultivation, shaking cultivation, and static cultivation.

<Oil or Fat Extracting Step>

In the present invention, the PL extracting step is carried out after carrying out the oil or fat extracting step for the cells collected in the lipid producing cell culturing step. The oil or fat extracting step is for producing defatted cells (residual cells) from the collected mass of cells, wherein an oil or fat such as triglycerides is extracted from the cells and removed. In this step, non-PL lipids are removed either entirely or partially without removing hardly any LCPUFA-PL. In other words, the oil or fat extracting step is the pre-step of the PL extracting step. It should be noted however that the oil or fat, such as triglycerides, extracted in the oil or fat extracting step contains LCPUFA as a constituent, and therefore has a good market value as a LCPUFA-containing oil or fat.

In the oil or fat extracting step, the collected cells may be used either directly as viable cells, or after sterilization. Further, the cells may be processed in the culture solution without being collected. Alternatively, the collected cells may be used either directly in the form of a cluster, or after they are processed into a plate, string, grain, powder, or any other form. The collecting method of cells is not particularly limited either. When the amount of cultured cells is small, centrifugation can be carried out using a common centrifuge. On the other hand, when the amount of collected cells is large, it is preferable that the cells be separated by continuous centrifugation, with or without filtration using a film, etc.

The collected cells may remain wet, or may be dried to obtain dried cells. In the present invention, use of dried cells is more preferable. In this way, an oil or fat can be efficiently extracted (see Examples). A method of drying the wet cells is not particularly limited. For example, conventional drying processes such as ventilation, a heat treatment, decompression, and lyophilization can be used.

Thus, after the lipid producing cell culturing step, a producing method of the present invention may include a cell collecting step of collecting cells, and a cell processing step of processing the collected cells. In the cell processing step, the collected cells may be processed into an arbitrary form, or wet cells may be dried to obtain dried cells.

In the oil or fat extracting step, a method of extracting oil or fat from the cells is not particularly limited, and a conventional extracting method can be used. Specifically, at least the following methods are available: compression extraction employing applied pressure; rendering extraction using hot water or steam; and extraction using various extractants.

The compression extraction employing applied pressure is not particularly limited as long as it can extract an oil component in the cells by applying pressure on the material used. For example, a method using a hydraulic press of a batch type, or a method using devices such as a continuous expeller can be used.

The rendering extraction is not particularly limited, and may be a dry type or wet type. Specifically, a dry type using direct fire, or steam rendering (wet type) by an autoclave are available.

To explain the dry type more specifically, oil or fat is liquidated by heating the cells under direct fire or jacket steam, for example. In steam rendering, specifically, the cells are exposed to heated steam. By heating and stirring, the oil component is obtained in the form of an emulsion, along with other components such as water and protein. With a centrifuge, the waste water is separated, and a crude oil is obtained with optional filtration. The conditions of steam rendering are not particularly limited. For example, elution may be carried out for 4 to 6 hours under the heated steam of 3 $kg/cm^2$ to 4 $kg/cm^2$.

The type of extractant used for the extraction is not particularly limited. Generally, an extract of at least one of an aliphatic organic solvent and water is used. Alternatively, a supercritical carbon dioxide gas may be used. Among such extracts, specific examples of aliphatic organic solvents include: saturated hydrocarbons such as hexane, petroleum ether (organic solvent including pentane and hexane as major components); ketones such as acetone; alcohols such as methanol, ethanol, propanol, and butanol; esters such as ethyl acetate; and halogenated hydrocarbons such as chloroform and dichloromethane. In the case of water, an aqueous solution dissolving a known solute may be used. These extracts may be used either alone or in a combination of two or more kinds. Among the extracts as exemplified above, saturated hydrocarbons such as hexane or petroleum ether are preferable, and hexane is more preferable, in order to efficiently remove oil or fat such as triglycerides.

The extraction process with the extractant may be carried out in a batch or continuously. The conditions of extraction with the extractant are not particularly limited either. The temperature, the amount of extractant used, and the time of extraction are suitably selected according to the type of extracted oil or fat such as triglycerides, and the amount of cells used (volume, weight). In the extraction, it is preferable that the cells be gently stirred by being dispersed in the extractant. In this way, the extraction can be carried out efficiently.

Note that, after the oil or fat extracting step, the resulting defatted cells may be directly used in the PL extracting step, or may be processed and stored for later use. As described above, the oil or fat extracting step is one of the producing steps of defatted cells, as well as a step of producing oil or fat, which itself has a market value. Thus, if the oil or fat is the required product, the defatted cells can be regarded as a waste. In this case, the byproduct defatted cells obtained in the production of oil or fat can be stored, and can be used as a raw material in the production according to the present invention. As such, the oil or fat extracting step is not necessarily required in the producing method of the present invention.

<PL Extracting Step>

In a producing method according to the present invention, the PL extracting step of extracting PL from defatted cells is essential. In the PL extracting step, the method of extracting PL from the defatted cells is not particularly limited. However, as in the oil or fat extracting step, it is preferable to use extraction with an extractant.

The extractant used to extract PL from the defatted cells is not particularly limited. As in the oil or fat extracting step, an extract of at least one of an aliphatic organic solvent and water, or supercritical carbon dioxide gas can be suitably used. Among such extracts, examples of aliphatic organic solvents include: saturated hydrocarbons such as hexane or petroleum ether (organic solvent containing pentane and hexane as major components); ketones such as acetone; alcohols such as methanol, ethanol, propanol, and butanol; esters such as ethyl acetate; halogenated hydrocarbons such as chloroform and dichloromethane; cyanized hydrocarbons such as acetonitrile; and ethers such as diethyl ether. In the case of water, an aqueous solution dissolving a known solute may be used. These extracts may be used either alone or in a combination of two or more kinds.

Among the extracts as exemplified above, preferable examples of aliphatic organic solvents include: saturated hydrocarbons, alcohols, a mixed solvent of saturated hydrocarbon and alcohol, and a mixed solvent of halogenated hydrocarbon and alcohol. As a saturated hydrocarbon, hexane is preferable. As an alcohol, ethanol is preferable. As a mixed solvent of saturated hydrocarbon and alcohol, a mixed solvent of hexane and ethanol is preferable. As a mixed solvent of halogenated hydrocarbon and alcohol, a mixed solvent of chloroform and methanol is preferable.

Among these organic solvents, hexane and/or ethanol are particularly preferable when used in food. When using a mixture of hexane and ethanol, it is preferable that the hexane:ethanol ratio of the mixture be 4:1 to 0:6 by volume, more preferably 4:1 to 1:4 by volume, and further preferably 4:1 to 2:4 by volume. In the event where the hexane:ethanol ratio is 0:6, an organic solvent with 100% ethanol is used. When a mixed solvent of hexane and ethanol, or ethanol is used, a small amount of water may be added.

The extraction process with the extractant may be carried out in a batch or continuously. The conditions of extraction with the extractant are not particularly limited either. The temperature, the amount of extractant used, and the time of extraction are suitably selected according to the type of PL to obtain, and the amount of cells used (volume, weight). In the extraction, it is preferable that the cells be gently stirred by being dispersed in the extractant. In this way, the extraction can be carried out efficiently.

<Other Steps>

As described above, a producing method according to the present invention at least includes the PL extracting step, and preferably includes the oil or fat extracting step. In addition, the method may also include other steps. Specific examples of such steps are the cell collecting step and cell processing step, as described above. Further, as will be described in later Examples, a PL purifying step of purifying the PL obtained in the PL extracting step may be additionally included.

A specific method by which the PL purifying step is carried out, i.e., a method of purifying the crude PL obtained in the PL extracting step is not particularly limited. In later Examples, PL is purified by thin layer chromatography (TLC) or acetone fractionation. However, the method is not just limited to this, and various solvent fractionating methods such as column chromatography can be used. The carrier used in the chromatography is not particularly limited, and conventional carriers can be suitably used. The solvent used in the solvent fractionation is not particularly limited either, and conventional solvents can be suitably used.

<Phospholipids According to the Present Invention>

Phospholipids according to the present invention are produced by the producing method described above. In other words, phospholipids according to the present invention are extracted from the defatted cells obtained by extracting TG-containing oil or fat from the lipid producing cells, and include LCPUFA as a constituent.

Phospholipids according to the present invention are not particularly limited as long as they include LCPUFA as a constituent, and may be any conventional phospholipids. Specific examples of such phospholipids include: glycerophospholipids such as phosphatidylcholine (PC), phosphatidylserine (PS), phosphatidylethanolamine (PE), phosphatidylinositol (PI), phosphatidylglycerol (PG), phosphatidic acid (PA), and cardiolipin (CL); sphingophospholipids such as sphingomyelin (SP); and lysophospholipids such as lysophosphatidylcholine (LPC), lysophosphatidylserine (LPS), lysophosphatidylethanolamine (LPE), lysophosphatidylinositol (LPI), lysophosphatidylglycerol (LPG) and lysophosphatidic acid (LPA). Among these phospholipids, PC, PS, PE, PI and phosphatidic acid are particularly preferable.

Phospholipids according to the present invention include at least one kind of phospholipids as exemplified above, and may include two or more kinds of phospholipids. In the case of crude phospholipids not purified by the purification step, various types of trace components may be added. An example of such trace components is a lipid component (oil or fat, etc.) other than the phospholipids derived from the lipid producing cells.

The constituent LCPUFA of phospholipids according to the present invention is not particularly limited as long as it is an unsaturated fatty acid having 20 or greater carbon atoms with a double bond. Specific examples of such unsaturated fatty acids include: eicosadienoic acid; eicosatrienoic acids such as dihomo-γ-linolenic acid and mead acid; eicosatetraenoic acids such as arachidonic acid (AA); eicosapentaenoic acid; docosadienoic acid; docosatrienoic acid; docosatetraenoic acid; docosapentaenoic acid; docosahexaenoic acid (DHA); tetracosadienoic acid; tetracosatrienoic acid; tetracosatetraenoic acid; tetracosapentaenoic acid; tetracosahexaenoic acid. Among these LCPUFA, arachidonic acid (AA) and/or docosahexaenoic acid (DHA) are preferable. Only one kind of LCPUFA, or two or more kinds of LCPUFA may be contained as constituents of the LCPUFA-PL.

In the LCPUFA, at least one of the C—C double bonds (—C=C—) in its structure may be conjugated. The conjugate double bonds may include a carbonyl group (C=O), or may be formed by adjacent C—C double bonds.

The proportion of LCPUFA with respect to total fatty acids contained in the LCPUFA-PL is not particularly limited, but is preferably 22 percent by weight or greater, more preferably 31 percent by weight or greater, and further preferably 37 percent by weight or greater. When arachidonic acid (AA) is contained as LCPUFA, the proportion of AA with respect to total fatty acids contained in the LCPUFA-PL is not particularly limited, but is preferably 0.3 percent by weight or greater, more preferably 5 percent by weight or greater, further preferably 20 percent by weight or greater, and particularly preferably 34 percent by weight or greater.

When the LCPUFA-PL is PC, the proportion of AA with respect to total fatty acids contained as constituents of the total PC is preferably 15 percent by weight or greater, or more preferably 40 percent or greater. When the LCPUFA-PL is PS, the proportion of AA with respect to total fatty acids contained as constituents of the total PS is preferably 5 percent by weight or greater, or more preferably 20 percent by weight or greater. In this way, phospholipids according to the present invention can provide superior products such as nutritional compositions.

Note that, regardless of the producing method used, phospholipids according to the present invention include LCPUFA-PL that contains at least PC and PS, and LCPUFA that contains at least AA. In such PC- PS-containing phospholipids with AA-containing LCPUFA, the proportion of AA with respect to total fatty acids contained as constituents of the total PC is 40 percent by weight or greater, and the proportion of AA with respect to total fatty acids contained as constituents of the total PS is 20 percent by weight or greater.

Further, phospholipids according to the present invention may include PC that contains DGLA as LCPUFA, and may additionally include PS that contains DGLA as LCPUFA. When the phospholipids include PC that contains DGLA as LCPUFA, the proportion of DGLA with respect to total fatty acids contained as constituents of the total PC is 3 percent by weight or greater. When the phospholipids additionally include PS that contains DGLA as LCPUFA, the proportion of DGLA with respect to total fatty acids contained as constituents of the total PS is 1 percent by weight or greater.

The PC and PS behave differently in the body and have distinct physiological functions. Thus, with the AA contained as LCPUFA, the combined effects in the body make phospholipids of the present invention even more desirable as nutritional compositions. Further, with AA or DGLA contained as LCPUFA, the properties and functions of these compounds make phospholipids of the present invention even more desirable as nutritional compositions.

The AA is one type of polyunsaturated fatty acid, and it constitutes about 10 percent of fatty acids in the blood or an important organ such as liver. More specifically, in the human blood, the composition ratios of fatty acids in the phospholipids are 11 percent AA, 1 percent eicosapentaenoic acid (EPA), and 3 percent DHA. The AA is an important constituent of the cell membrane, and is involved in the regulation of fluidity in the cell membrane. Various functions of AA in the body metabolism are known. It is also known that the AA serves as an important direct precursor of prostaglandins.

Further, in recent years, the role of AA as a nutriment for infants has caught the attention. The AA is also the subject of study as a constituent fatty acid of endogenous cannabinoid (2-arachidonoyl monoglycerol, anandamide) that has neuroactive effects. Generally, ingestion of food rich in linoleic acid produces AA in the body through conversion. However, in infants, elderly, and the patients or potential patients of common adult diseases, the catalytic action of enzymes involved in the biosynthesis of AA is weak, and the AA tends to be deficient. Therefore, direct intake of AA is desired.

As with AA, the DGLA is also one type of polyunsaturated fatty acid, and it constitutes the fatty acids in the blood and important organs such as liver. In humans and other organisms, the composition ratio of DGLA is about several percent with respect to total fatty acids. Further, as with AA, the DGLA is also involved in the regulation of fluidity in the cell membrane. Various functions of DGLA in the body metabolism are known. It is also known that the DGLA serves as an important direct precursor of prostaglandins. More specifically, it is known that series 1 prostaglandins is produced from DGLA.

Particularly, various actions of series 1 prostaglandins produced from DGLA have been under study, including, for example, platelet aggregate suppressing action, vasodilating action, broncodilating action, and anti-inflammatory action. Generally, DGLA is converted from linoleic acid. However, as with AA, DGLA becomes deficient when the activities of enzymes involved in the DGLA biosynthesis are weak. Therefore, direct intake is also desirable for DGLA.

As described above, phospholipids according to the present invention include at least PC and PS as LCPUFA-PL, and additionally include at least a certain amount of AA as a constituent of PC and PS. The phospholipids of the invention are therefore highly desirable as nutritional compositions.

(II) Lipid Composition According to the Present Invention, and Producing Method Thereof The composition, state, or other conditions of a lipid composition according to the present invention are not particularly limited as long as the lipid composition includes phospholipids according to the present invention. In one preferable composition, at least LCPUFA-PL is dissolved as a solute in a liquid lipid used as a solvent, wherein the liquid lipid contain LCPUFA as a constituent (LCPUFA lipid). That is, one example of a lipid composition according to the present invention is a phospholipids solution in which LCPUFA-PL is dissolved in a liquid LCPUFA lipid.

<Absorption of LCPUFA-PL Contained in a Phospholipid Solution>

In a highly purified form, phospholipids exist as a powder, and is generally very hygroscopic and easily degradable (See Biochemistry Experiment Lecture 3, Science of Lipids, pp. 22-23, Tokyo Kagaku Dojin Co., Ltd. (1974)). Therefore, for ease of handling, phospholipids are often dissolved in a small amount of liquid lipid used as a solvent (phospholipid solution). As the liquid lipid used as a solvent, triglycerides (TG) etc. can be suitably used.

With the LCPUFA-PL prepared in a phospholipid solution, degradation of LCPUFA-PL can be effectively prevented for better handling. However, when taken as food, efficient uptake of LCPUFA-PL is often prevented. Specifically, as described in the BACKGROUND ART section, the phospholipids in the digestive tract are absorbed in the form of lysophospholipids, and reassembled into phospholipids in the small intestine. Here, when the phospholipids are ingested as a phospholipids solution, the acyl group generated during the reassembly of phospholipids from lysophospholipids includes both LCPUFA derived from LCPUFA-PL, and fatty acids derived from the liquid lipid.

The TG generally used as the liquid lipid usually contain LCPUFA as a constituent, but the concentration of LCPUFA is generally low. As such, the fatty acids providing the acyl group also include fatty acids other than LCPUFA ("non-LCPUFA fatty acids" hereinafter).

Thus, when the liquid lipid used as a solvent contain only a small amount of LCPUFA, a large amount of non-LCPUFA fatty acid is used during the reassembly of phospholipids from lysophospholipids. As a result, the actual amount of absorbed LCPUFA-PL is greatly reduced even when high-quality LCPUFA-PL is ingested as phospholipids.

It is therefore highly preferable that the liquid lipid be a LCPUFA lipid, such as TG, that contain a large amount of LCPUFA as a constituent, because it allows the LCPUFA-PL to be efficiently absorbed. As such, the present invention is adapted to provide a lipid composition in which the LCPUFA-PL is dissolved in a liquid LCPUFA lipid.

<Components of the Lipid Composition>

The liquid LCPUFA lipid used as a solvent of the phospholipids solution are not particularly limited. For example, triglycerides, diglycerides, monoglycerides, fatty acids, and fatty acid alcohol ester can be used. Further, various types of LCPUFA described in the <Phospholipids according to the present invention> section can be used as the LCPUFA contained as a constituent of the LCPUFA lipid. Because the fatty acids can be directly used as the LCPUFA lipid, the liquid LCPUFA themselves can be used as the LCPUFA lipid.

As will be described later, TG-containing oil or fat obtained in the oil or fat extracting step of a producing method according to the present invention can be used as the LCPUFA lipid. The oil or fat, such as triglycerides, obtained by the oil or fat extracting step of the present invention can be suitably used as the LCPUFA oil or fat, because it contains LCPUFA as a constituent.

The proportion of LCPUFA with respect to total fatty acids in the LCPUFA lipid is not particularly limited, but is preferably 11 percent by weight or greater, more preferably 25 percent or greater, and even more preferably 27 percent or greater. When arachidonic acid (AA) is contained as LCPUFA, the proportion of arachidonic acid with respect to total fatty acids contained in the LCPUFA lipid is not particularly limited, but is preferably 9 percent by weight or greater, or more preferably 20 percent or greater. The upper limit is not particularly limited but should be as high as possible.

When the proportion of LCPUFA with respect to total fatty acids is in these ranges, the LCPUFA content in the total fatty acids will not decrease, or decreases only slightly, with respect to the lipid composition as a whole. In other words, the LCPUFA content in the liquid lipid which coexists with the LCPUFA-PL can be increased. In this way, when absorbed in the small intestine, a large amount of LCPUFA will be able to provide the acryl group during the reassembly of phospholipids from the lisophospholipids. As a result, the amount of actually absorbed LCPUFA-PL will not decrease, or decreases only slightly.

The LCPUFA-PL is generally a powder, and is very hygroscopic and easily degradable. However, by providing the LCPUFA-PL as a phospholipid solution, it is not required to take into account these hygroscopic and degradable properties of LCPUFA-PL. Further, with the LCPUFA-PL in the form of a liquid, overall handling can be further improved.

As the phospholipids used as a solute, phospholipids according to the present invention are used, i.e., phospholipids obtained by a producing method according to the present invention. However, in the present invention, a fat-soluble substance other than phospholipids may also be included as a solute.

Non-limiting examples of such fat-soluble substances include: sterols, sterol esters, glycolipids, sphingolipids, waxes, pigments, carotenoids, and tocopherols. A fat-soluble substance is suitably selected according to intended use of a lipid composition according to the present invention.

Various additives may be added to a lipid composition according to the present invention. Non-limiting examples of additives include: vitamin E, tocotrienol, sesamin, sesaminol, sesamol, astaxanthin, astaxanthin esters, sterols, and carotenes. Many of additives as exemplified above are already included in the fat-soluble composition. However, the additives added to the fat-soluble composition are not necessarily required to be fat soluble. A lipid composition according to the present invention can be used as a nutritional composition in food etc. As such, the invention can use all additives that can be added to food.

<Producing Method of the Lipid Composition>

A producing method of the lipid composition is not particularly limited. In the invention, phospholipids obtained by a producing method of phospholipids according to the present invention are dissolved in liquid LCPUFA lipid, and optionally, other components are added and dissolved or dispersed. In other words, a producing method of a lipid composition according to the present invention at least includes the PL extracting step, and also includes a solution preparing step of preparing a phospholipid solution by dissolving the PL-containing LCPUFA-PL obtained in the PL extracting step in the LCPUFA lipid.

Further, in a lipid composition according to the present invention, the oil or fat obtained in the oil or fat extracting step can be suitably used as the LCPUFA lipid. As such, a producing method of a lipid composition according to the present invention may include an oil or fat extracting step.

By controlling the procedure of extracting oil or fat such as triglycerides in the oil or fat extracting step, or the procedure of extracting LCPUFA-PL in the PL extracting step, a lipid composition according to the present invention can be produced more easily. Specifically, by suppressing the extent to which the oil or fat is removed (extracted) from the lipid producing cells, the composition of lipids remaining in the resulting defatted cells can be varied.

The extent of removal is not particularly limited, and extraction conditions are suitably selected according to various prerequisites such as the composition of the lipid composition, type of lipid producing cells, or the extraction method used to remove oil or fat from the cells. For example, when an aliphatic organic solvent is used as an extractant, conditions such as the amount of organic solvent, the number of extraction processes, and extraction temperature are varied in the oil or fat extracting step. In this way, liquid oil or fat such as triglycerides (TG) can remain in the phospholipids obtained in the PL extracting step. Further, since the remaining liquid oil or fat is a LCPUFA lipid whose constituent is LCPUFA, a lipid composition can be readily obtained. Thus, in the present invention, by suppressing the amount of extracted oil or fat in the oil or fat extracting step, a lipid composition can be extracted as a phospholipid solution in the PL extracting step. In other words, the lipid composition as a phospholipids solution can be easily produced by varying conditions of the oil or fat extracting step in a producing method of phospholipids according to the present invention.

In a lipid composition according to the present invention, the two primary components, LCPUFA-PL and LCPUFA lipid, can be mixed at any proportions. As such, the amount of LCPUFA lipid is not particularly limited as long as it can achieve the required fluidity for improved handling of the phospholipid solution.

Further, in order to adjust the concentrations of the primary components, a lipid composition according to the present invention may include lipids other than the lipids obtained by processes in a producing method according to the present invention, i.e., the LCPUFA, or the oil or fat obtained from the lipid producing cells used as a starting material. As such lipids, any of LCPUFA-PL, non-LCPUFA, and LCPUFA lipid can be added.

Note that, a lipid composition according to the present invention is not just limited to the phospholipid solution used for improved handling, and any other composition may be used. Further, since the lipid composition prepared as a phospholipid solution is dissolved mostly for improved handling of the LCPUFA-PL, the lipid composition can be directly used as phospholipids.

(III) Use of the Present Invention

The use of the present invention is not particularly limited. As a representative example, phospholipids or a lipid composition according to the present invention can be used as a nutritional composition for supplying LCPUFA-PL. The organism for which the nutritional composition is used is not particularly limited. Human is a representative example. Other examples are domestic animals and test animals. The nutritional composition may be ingested in any manner, but oral administration is most preferable. Thus, the present invention includes food that includes the phospholipids or lipid composition.

Food according to the present invention is not particularly limited as long as phospholipids or a lipid composition according to the present invention is included. Non-limiting examples include: bread, sweets of various kinds (including cold or frozen sweets), prepared food, dairy products, cereals, tofu, fried tofu, noodles, box lunch, seasonings, agricultural products such as wheat flour or meat, preserved food (canned food, frozen food, retort-packed food, etc.), soft drinks, milk beverage, soy milk, soups such as potage soup, and all other common foods. A method by which the phospholipids or lipid composition are added to these common foods is not particularly limited, and any conventional method can be suitably used depending on the type of food used.

Further, food according to the present invention includes functional foods used for specific purposes, such as health foods or nutriments. Specific examples include nutraceutical foods including various supplements, and specified health foods. For ease of handling, it is preferable that phospholipids according to the present invention be prepared as a phospholipid solution. However, in the case of supplements, the phospholipid solution (lipid composition) can be directly used only by processing it into appropriate form. In this case, the form of the phospholipid solution is not particularly limited. Specifically, a lipid composition (or food) according to the present invention may be in the form of a liquid, powder, or capsule (see Example 6 to be described later). Alternatively, a lipid composition according to the present invention may be in the form of a pill or tablet. In using phospholipids or a lipid composition according to the present invention, all techniques such as dissolving in common oil- or fat-containing food, or powderization, applicable for common oil or fat, can be used.

Use of the present invention includes using phospholipids obtained by the producing method. Thus, when phospholipids or a lipid composition according to the present invention are used as food etc. with the addition of other components, the additional components may be solubilized in the form of a liposome, using the phospholipids. In this case, a dispersion liquid of an oil-in-water (O/W) type with a liposome can be used as a composition according to the present invention.

As described above, in the present invention, the LCPUFA-PL can be efficiently and stably obtained from the lipid producing cells obtained by fermentation of microorganisms. Conventionally, animal organs such as the cow brain have been the major source of LCPUFA-PL. However, with the epidemic of the mad cow disease, these conventional sources have been avoided. The present invention, on the other hand, relies on fermentation techniques to obtain LCPUFA-PL. This is advantageous in terms of customer acceptance, making the present invention particularly suitable when the phospholipids or lipid composition are used in common foods or functional foods.

The applicable field of the invention is not just limited to food, but the invention is also applicable in the field of medicine. That is, phospholipids or a lipid composition according to the present invention may also be used as medicines. In this case, the invention is not just limited to a particular application, and any conventional technique may be used depending on the intended use.

EXAMPLES

The following will describe the present invention in more detail based on Examples. It is to be noted that the invention is not limited in any way by the following Examples. The culture media used in the Production Examples 1 through 5 in producing dried cells and defatted cells are described in detail in the following section "Preparation of Culture Media."

[Preparation of Culture Media]

The composition of seed culture medium A used in the Production Example 1 for producing dried cells and defatted cells, was 1% yeast extract, 2% glucose, and the remaining being water. The media was adjusted to pH 6.3. Similarly, the composition of seed culture medium B was 1% yeast extract, 2% glucose, 0.1% soy bean oil and the remaining being water. The media was adjusted to pH 6.3. For the main culture medium C, culture medium C-b was added to culture medium C-a. The main culture medium C was prepared with pH 6.1. The culture medium C-a was prepared such that 336 kg of a soy bean powder, 16.8 kg of $KH_2PO_4$, 2.8 kg of $MgCl_2.6H_2O$, 2.8 kg of $CaCl_2.2H_2O$, and 56 kg of soy bean oil were added to water, and stirred. The solution was adjusted to 4500 L of final volume by adding water, and subsequently was sterilized at 121° C. for 20 minutes. The culture medium C-b was prepared such that 112 kg of hydrous glucose was added to water, and stirred. The solution was adjusted to 1000 L of final volume by adding further water, and subsequently was sterilized at 140° C. for 40 seconds.

The composition of the culture medium D used in the Production Examples 2 through 5 for producing dried cells and defatted cells was 1.8% glucose, 1.5% soy bean powder, 0.1% soy bean oil, 0.3% $KH_2PO_4$, 0.1% $Na_2SO_4$, 0.05% $CaCl_2.2H_2O$, 0.05% $MgCl_2.6H_2O$, and the remaining being water. The culture medium D was adjusted to pH 6.3.

Production Example 1 for Producing Dried Cells and Defatted Cells

As the lipid-producing cells, *Mortierella alpina* CBS754.68 was used as one of the arachidonic acid-containing phospholipid producing cells. A strain in custody of CBS754.68 was inoculated to the seed culture medium A. The seed culture (the first step) started with shaking at 100 rpm and 28° C. It was continued for three days. Subsequently 30 L of culture medium B was prepared in an aerated stirring culture bath of 50 L. To the culture medium B, the seed culture (the first step) was inoculated. Seed culture (the second step) was started with stirring frequency of 200 rpm and with the pressure in the bath of 150 kPa at 28° C. It was continued for 2 days.

Next, the seed culture (the second step) was inoculated to the main culture medium C prepared up to 5600 L in the culture bath of 10 kL volume. The main culture was started at a temperature of 26° C., with aerated volume of 49 $Nm^3/hr$ and with an internal pressure of 200 kPa. After an adequate time had passed, the culture feeding, in which an adequate amount of hydrous glucose was added, was suitably conducted. As the culture feeding, a total of 1454 kg of hydrous glucose was added six times. Thus the main culture was continued for 306 hours.

After the main culture, the cells culture media were sterilized at 120° C. for 20 minutes, and then the wet cells were collected from the media by a hydro-extractor of continuous type. The wet cells were dried by a fluidized-bed vibrating dryer so as to obtain dried cells dried up to 1% by weight of water. The dried cells were transported by a pneumatic transporter to a filling position, was filled with nitrogen gas into a 1 $m^3$ container bag made of aluminum pouch with its opening heat sealed after the filling, and then stored in a refrigeration cabinet at 10° C. or below.

Three liter of hexane was added to 1 kg of the dried cells taken from the container bag. After the mixture was stirred gently at room temperature for 15 hours, the hexane layer was removed by filtration. From the obtained dried cells, residual hexane was removed by aeration so as to obtain the defatted cells A-1. To the defatted cells A-1, 3 L of hexane was added again. After stirring gently for three hours at room temperature, and subsequent similar operation as the aforementioned operation, the defatted cells A-2 were obtained.

After the second extraction process of hexane, 3 L of hexane was added again to the defatted cells A-2. After stirring gently for three hours at room temperature, and subsequent similar operation as the aforementioned operation, the defatted cells A-3 were obtained. Again, 3 L of hexane was added to the defatted cells A-3. After stirring gently for three hours at room temperature, and subsequent similar operation as the aforementioned operation, the defatted cells A-4 were obtained.

In the four extraction processes of hexane, the extracted lipid in any of the collected hexane layers was almost exclusively triglycerides. Phospholipids were not detected in these layers.

Production Example 2 for Producing Dried Cells and Defatted Cells

Five liters of main culture medium D was prepared in a 10 L aerated stirring culture bath and then sterilized. As lipid-producing cells, *Mortierella polycephala* IFO6335, a filamentous bacteria to produce arachidonic acid, was inoculated and cultured at 26° C., with an aerated volume of 1 vvm and with the stirring frequency of 300 rpm. The culturing was continued for 9 days. Depending on the consumption of glucose, 1% glucose was suitably added. The cultured cells were sterilized in a similar manner as in the Example 1 and were dried after the culture medium was removed so as to obtain dried cells.

To 40 g of the dried cells, 120 mL of hexane was added. After the mixture was stirred gently at room temperature for 3 hours, the hexane layers were removed by filtration. Then, 120 mL of hexane was added to the obtained cells again. After stirring gently for 15 hours at room temperature, the hexane layers were removed by filtration. From the obtained dried cells from which hexane was extracted, residual hexane was removed by aeration so as to obtain the defatted cells B.

In the hexane layers collected in the extraction process of hexane, the extracted lipid was almost exclusively triglycerides. Phospholipids were not detected in these layers.

Production Example 3 for Producing Dried Cells and Defatted Cells

Except that *Mortierella elongata* SAM1860 (International Deposit No. FERMBP-3589 based on Budapest Treaty), a filamentous bacteria to produce dihomo-γ-linolenic acid (DGLA), was inoculated as lipid-producing cells, the similar procedure as in the Production Example 2 were conducted so as to obtain the defatted cells C.

In the hexane layers collected in the extraction process of hexane, the extracted lipid was almost exclusively triglycerides. Phospholipids were not detected in these layers.

Production Example 4 for Producing Dried Cells and Defatted Cells

Except that *Mortierella alpina* SAM2086 (International Deposit No. FERMBP-15766 based on Budapest Treaty), filamentous bacteria to produce mead acid, were inoculated as lipid-producing cells, a similar procedure as in the Production Example 2 was conducted so as to obtain the defatted cells D.

In the hexane layers collected in the extraction process of hexane, the extracted lipid was almost exclusively triglycerides. Phospholipids were not detected in these layers.

Production Example 5 for Producing Dried Cells and Defatted Cells

Except that *Echinosporangium transversalis* ATCC16960, filamentous bacteria to produce arachidonic acid, were inoculated as lipid-producing cells, a similar process as in the Production Example 2 was conducted so as to obtain the defatted cells E.

In the hexane layers collected in the extraction process of hexane, the extracted lipid was almost exclusively triglycerides. Phospholipids were not detected in these layers.

Production Example 6 for Producing Dried Cells and Defatted Cells

Except that the culture time period was 6 days, a similar process as in the Production Example 2 was conducted so as to obtain dried cells *Mortierella polycephala* IFO6335. In addition, except that the amount of the dried cells was 20 g and that the hexane volume was 60 mL, a similar process as in the Production Example 2 was conducted to obtain the defatted cells F, *Mortierella polycephala* IFO6335.

In the hexane layers collected in the extraction process of hexane, the extracted lipid was almost exclusively triglycerides. Phospholipids were not detected in these layers.

Production Example 7 for Producing Dried Cells and Defatted Cells

Except that the culture time period was 6 days, a similar process as in the Production Example 5 was conducted to obtain dried cells of *Echinosporangium transversalis* ATCC16960. In addition, except that the amount of the dried cells was 20 g and that the hexane volume was 60 mL, a similar process as in the Production Example 2 was conducted to obtain the defatted cells G, *Echinosporangium transversalis* ATCC 16960.

In the hexane layers collected in the extraction process of hexane, the extracted lipid was almost exclusively triglycerides. Phospholipids were not detected in these layers.

Example 1

Extraction of Phospholipids Containing Arachidonic Acid from the Defatted Cells A-2

Twenty five mL of various organic solvents were added as extractant to one gram of the defatted cells A-2 obtained in the Production Example 1 for producing dried cells and defatted cells. The mixture was stirred gently at 60° C. for one hour. As an extraction media, hexane, mixed solvents of hexane and ethanol (a to e), ethanol, a mixed solvent of chloroform or methanol was used. The composition of these extraction media (mixing ratio by volume) is shown in Table 1.

TABLE 1

| Extractant | Compositions (mixing ratio by volume) |
|---|---|
| Hexane | Hexane:Ethanol = 6:0 |
| Mixed solvent of hexane and ethanol (a) | Hexane:Ethanol = 4:1 |
| Mixed solvent of hexane and ethanol (b) | Hexane:Ethanol = 4:2 |
| Mixed solvent of hexane and ethanol (c) | Hexane:Ethanol = 3:3 |
| Mixed solvent of hexane and ethanol (d) | Hexane:Ethanol = 2:4 |
| Mixed solvent of hexane and ethanol (e) | Hexane:Ethanol = 1:4 |
| Ethanol | Hexane:Ethanol = 0:6 |
| Mixed solvent of chloroform and methanol | Chloroform:Methanol = 2:1 |

In either case, after the layers of the organic solvent were filtrated, collected and subsequently the organic solvent was removed so as to obtain a crude phospholipid fraction. The obtained phospholipid fraction was fractionated into triglycerides (TG) and phospholipids (PL) by thin-layer chromatography with silica gel (TLC). A mixed solvent of hexane and ethyl ether with the mixing ratio of 7:3 was used as a developing solvent. Both fractions were scratched and the fatty acids were qualified and quantified by inducing the fractions toward methyl ester by way of methanol hydrochloride method. Pentadecanoic acid was used as an internal reference. The result of the qualification and quantification of the fatty acids is shown in the Table 2.

TABLE 2

| Extractant | Lipids as extracted fatty acids(m/g defatted cells) | | Content of LCPUFA in total fatty acids of PL | |
|---|---|---|---|---|
| | PL | TG | AA | DGLA |
| Hexane | 0.0 | 35.0 | — | — |
| Mixed solvent of hexane and ethanol (a) | 20.0 | 40.0 | 43.0 | 2.6 |
| Mixed solvent of hexane and ethanol (b) | 24.4 | 40.4 | 43.7 | 2.5 |
| Mixed solvent of hexane and ethanol (c) | 24.1 | 43.4 | 42.5 | 2.5 |
| Mixed solvent of hexane and ethanol (d) | 19.9 | 45.2 | 42.7 | 2.6 |
| Mixed solvent of hexane and ethanol (e) | 16.4 | 41.8 | 42.5 | 2.6 |
| Ethanol | 16.3 | 42.0 | 41.7 | 2.6 |
| Mixed solvent of chloroform and methanol | 24.9 | 66.1 | 40.4 | 2.5 |

In the case where only hexane was used as extractant, the phospholipids were not extracted. In other cases, on the other hand, a remarkable amount of phospholipids was extracted. In addition, not less than 40% of the total fatty acids in the phospholipids were LCPUFA such as arachidonic acid (AA) or dihomo-γ-linolenic acid (DGLA). Eicosapentaenoic acid (EPA), on the contrary, was not detected.

Example 2

Extraction of Phospholipids Containing Arachidonic Acid from the Defatted Cells A-1 Through A-4

One liter of a mixed solvent of hexane and ethanol (mixing ratio of 1:1 by volume) was added to 200 grams of the defatted cells A-1 through A-4 obtained in the Production Example 1 for producing dried cells and defatted cells, respectively. The mixtures were stirred gently at 60° C. for 90 minutes. After filtration of the solvent layers, the same operation was repeated twice. All of the organic solvent layers were then collected and removed so as to obtain a crude phospholipid fraction. The obtained phospholipid fraction were fractionated into TG and PL by thin-layer chromatography with silica gel (TLC), similarly as in the Example 1, so as to conduct qualification and quantification of the fatty acids. The result of the qualification and quantification is shown in Table 3. The weight in Table 3 indicates the amount per 1 g of the defatted cells.

The crude phospholipid fraction obtained from the defatted cells A-2 was dissolved in cold acetone at 4° C., insoluble acetone constituent was collected twice so as to obtain the purified phospholipid fraction. The purified phospholipid fraction did not contain neutral lipids. In addition, the ratio of AA and DGLA in the total fatty acid was 43.4% and 2.6% respectively.

Further the purified phospholipid fraction was fractionated by thin-layer chromatography with silica (TLC) into phosphatidylcholine (PC), phosphatidylethanolamine (PE), phosphatidylserine (PS), phosphatidylinositol (PI) and glycolipids (GL), and then the qualification and quantification of the fatty acids were conducted. A mixed solvent of chloroform, methanol, acetic acids and water with the mixing ratio of 100:75:7:4 was used as a developing solvent. The composition of the obtained purified phospholipids is shown in Table 4.

TABLE 4

| Fraction | Percent by weight as fatty acids (%) | Content of LCPUFA in total fatty acids in each fraction (%) | |
|---|---|---|---|
| | | AA | DGLA |
| PC | 58.9 | 53.7 | 3.1 |
| PE | 25.1 | 33.9 | 1.7 |
| PS | 3.1 | 23.5 | 1.4 |
| PI | 5.4 | 22.2 | 3.3 |
| GL | 7.5 | 18.3 | 1.4 |

Example 3

Extraction of Phospholipids Containing PUFA from the Defatted Cells B Through E

Twenty five mL of a mixed solvent of hexane and ethanol (mixing ratio of 1:1 by volume) was added to 5 grams of the defatted cells B through E obtained in the Production Examples 2 through 5 for producing dried cells and defatted cells, respectively. The mixtures were stirred gently at 60° C. for 90 minutes. After the layers of the organic solvent were filtrated, the same operation was repeated twice. All of the layers of the organic solvent were then collected and removed so as to obtain a crude phospholipid fraction. The obtained phospholipids were fractionated, similarly as in Example 1, into TG and PL by thin-layer chromatography with silica gel (TLC) so as to conduct qualification and quantification of the fatty acids. The result of the qualification and quantification is shown in Table 5. The weight in Table 5 indicates the amount of the defatted cells per 1 g.

TABLE 3

| Defatted cells | Fraction | Lipids as extracted fatty acids (mg) | Content of LCPUFA in total fatty acids in each fraction (%) | | | LCPUFA in the extracted lipids (mg) | | |
|---|---|---|---|---|---|---|---|---|
| | | | AA | DGLA | Total | AA | DGLA | Total |
| A-1 | PL | 22.4 | 42.5 | 2.5 | 45.0 | 9.52 | 0.56 | 10.1 |
| | TG | 98.3 | 42.0 | 2.5 | 44.5 | 41.3 | 2.46 | 43.8 |
| A-2 | PL | 23.0 | 42.5 | 2.6 | 45.1 | 9.78 | 0.60 | 10.4 |
| | TG | 46.2 | 42.0 | 2.5 | 44.5 | 19.4 | 1.16 | 20.6 |
| A-3 | PL | 23.0 | 42.5 | 2.6 | 45.1 | 9.78 | 0.60 | 10.4 |
| | TG | 26.8 | 41.8 | 2.5 | 44.3 | 11.2 | 0.67 | 11.9 |
| A-4 | PL | 22.8 | 42.4 | 2.6 | 45.0 | 9.67 | 0.59 | 10.3 |
| | TG | 19.7 | 40.9 | 2.5 | 43.4 | 8.06 | 0.49 | 8.55 |

TABLE 5

| Defatted cells | Fraction | Lipids as extracted fatty acids (mg) | Content of LCPUFA in total fatty acids in each fraction (%) | | | | LCPUFA in the extracted lipids (mg) |
|---|---|---|---|---|---|---|---|
| | | | AA | DGLA | Mead acid | Total LCPUFA | |
| B | PL | 20.0 | 20.2 | 2.3 | 0.0 | 22.5 | 4.50 |
|   | TG | 50.2 | 9.6 | 1.9 | 0.0 | 11.5 | 5.77 |
| C | PL | 22.2 | 0.3 | 45.6 | 0.0 | 45.9 | 10.2 |
|   | TG | 43.0 | 0.0 | 35.7 | 0.0 | 35.7 | 15.4 |
| D | PL | 22.3 | 0.0 | 0.0 | 31.1 | 31.1 | 6.94 |
|   | TG | 42.0 | 0.0 | 0.0 | 25.8 | 25.8 | 10.8 |
| E | PL | 21.5 | 34.7 | 3.1 | 0.0 | 37.8 | 8.13 |
|   | TG | 42.5 | 20.0 | 2.5 | 0.0 | 22.5 | 9.56 |

Example 4

Production of Purified LCPUFA-PL

Fifty mL of a mixed solvent of hexane and ethanol (mixing ratio of 1:1 by volume) was added to 10 grams of the defatted cells F and G obtained in the Production Examples 6 and 7 for producing dried cells and defatted cells, respectively. The mixture was stirred gently at 60° C. for 90 minutes. After the solvent layers were filtrated, the same operation was repeated further twice. All of the solvent layers were then collected and removed so as to obtain a crude phospholipid fraction. The obtained crude phospholipid fraction was dissolved in cold acetone at 4° C., and insoluble acetone constituent was collected twice so as to obtain the purified phospholipid fraction. The purified phospholipid fraction did not contain neutral lipids. The purified phospholipid fraction was fractionated by a thin-layer chromatography with silica gel (TLC) into phosphatidylcholine (PC), phosphatidylethanolamine (PE), phosphatidylserine (PS), phosphatidylinositol (PI) and glycolipids (GL), and then the qualification and quantification of the fatty acids were conducted. A mixed solvent of chloroform, methanol, acetic acids and water with the mixing ratio of 100:75:7:4 was used as a developing solvent.

The composition of the purified phospholipids obtained from the defatted cells F is shown in Table 6, while the composition of the purified phospholipids obtained from the defatted cells G is shown in Table 7.

TABLE 6

| Fraction | Percent by weight as fatty acids (%) | Content of LCPUFA in total fatty acids in each fraction (%) | |
|---|---|---|---|
| | | AA | DGLA |
| PC | 56.2 | 30.0 | 3.1 |
| PE | 28.5 | 15.8 | 2.2 |
| PS | 10.2 | 15.6 | 1.1 |
| PI | 4.4 | 11.6 | 1.9 |
| GL | 0.7 | 8.5 | 1.3 |

TABLE 7

| Fraction | Percent by weight as fatty acids (%) | Content of LCPUFA in total fatty acids in each fraction (%) | |
|---|---|---|---|
| | | AA | DGLA |
| PC | 60.2 | 17.9 | 2.1 |
| PE | 23.1 | 10.0 | 1.7 |
| PS | 12.2 | 8.8 | 1.0 |

TABLE 7-continued

| Fraction | Percent by weight as fatty acids (%) | Content of LCPUFA in total fatty acids in each fraction (%) | |
|---|---|---|---|
| | | AA | DGLA |
| PI | 3.2 | 9.5 | 0.9 |
| GL | 1.3 | 8.5 | 1.1 |

Example 5

Encapsulation with LCPUFA-Containing Phospholipids

A 100:35 mixture (weight ratio) of gelatin (Nitta Gelatin Inc.) and food-additive glycerin (Kao Corporation) was prepared and water was added thereto. By dissolving the solution at 50° C. to 60° C., a gelatin coat with a viscosity of 2,000 cp was prepared.

Next, a crude phospholipid fraction, which was obtained from the defatted cells A-2 in the Example 2, and a vitamin E oil (Eisai Co., Ltd.) was mixed at a weight ratio of 100:0.05 so as to prepare the product 1.

Also a crude phospholipid fraction, which was obtained from the defatted cells A-2 in the Example 2, a purified phospholipid fraction extracted from salmon eggs (the ratio of DHA in the total fatty acids was 25%), soy bean oil (SHOWASANGYO Co., Ltd.) and a vitamin E oil (Eisai Co., Ltd.) was mixed at a weight ratio of 50:50:50:0.05 so as to prepare the product 2.

By using the products 1 and 2, encapsulation and drying was conducted by a known method to produce a soft capsule containing 180 mg of the product pro grain. Either soft capsule was suitable for oral ingestion.

Example 6

Preparation of Drinks with LCPUFA-Containing Phospholipids

The crude phospholipid fraction, which was obtained from the defatted cells A-2 in the Example 2 was stirred in water at 60° C. for 5 to 30 minutes, using a mixing-and-dispersing device (the Mtechnique product, CLEARMIX). As a result, a solution with dispersed liposome being uniformly dispersed in water was obtained. The concentration of phospholipids in the solution with dispersed liposome was from 0.1% to 20% and was controllable freely.

The average grain diameter of liposome in the solution with dispersed liposome was from about 50 nm to about 100 nm. The solution with dispersed liposome containing 10% phospholipids was added to orange juice, carbonated water, coffee, milk, soy milk, and a potage soup, each in 1/100 (v/v), so as to prepare (produce) drinks as the food of the present invention. These drinks were suitable for oral ingestion.

The invention being thus described, it will be obvious that the same way may be varied in many ways. Such variations were not to be regarded as a departure from the spirit and scope of the invention, and all such modifications as would be obvious to one skilled in the art are intended to be included within the scope of the following claims.

INDUSTRIAL APPLICABILITY

In a producing method of phospholipids according to the present invention, PL is extracted from defatted cells obtained by extracting oil or fat whose major component is TG from lipid producing cells, so as to efficiently produce LCPUFA-PL. The lipid producing cells can be cultured for mass production, and therefore can be effectively used as a supply source.

Conventionally, the LCPUFA-PL are obtained only in a small quantity from limited sources, and as such the supply and quality of LCPUFA-PL are unstable. With the present invention, however, the LCPUFA-PL can be stably provided in a mass quantity and with a good quality. With the epidemics of various diseases such as the mad cow disease, use of animal organs such as the cow brain has been practically impossible. It is therefore very meaningful, as in the present invention, to secure a stable supply source of LCPUFA-PL that are safe to use.

The defatted cells are the by-product of the step in which oil or fat such as TG is extracted from cells. Conventionally, the defatted cells have been disposed as a waste, or, at best, used as animal feedings, as with residues of common microbial fermentation. The present invention, on the other hand, uses the defatted cells as the practical supply source of LCPUFA-PL. The invention therefore enables the LCPUFA-PL to be produced at relatively low cost, in addition to effectively using the "waste" defatted cells.

Phospholipids according to the present invention can be handled with ease when provided as a solution using a liquid LCPUFA lipid as a solvent (lipid composition). Alternatively, the phospholipids can be directly used in food, so as to allow for efficient uptake of LCPUFA-PL. When the liquid LCPUFA lipid is oil or fat such as TG obtained in the oil or fat extracting step in particular, a high-quality lipid composition can be efficiently obtained.

The present invention therefore enables LCPUFA-PL to be produced both efficiently and stably, and thereby provides LCPUFA-PL at low cost while ensuring stable supply and quality.

As described above, the present invention efficiently and stably produces LCPUFA-PL by fermentation techniques. The present invention is therefore applicable not only to industries dealing with functional food but also in industries dealing with food in general and even medicines.

The invention claimed is:

1. Phospholipids (LCPUFA-PL) including a long-chain polyunsaturated fatty acids (LCPUFA) as constituents,
    wherein the LCPUFA-PL includes at least phosphatidylcholine and phosphatidylserine, and the LCPUFA includes at least arachidonic acid, and
    wherein a proportion of arachidonic acid with respect to total fatty acids contained as constituents of total phosphatidylcholine is 40 percent by weight or greater, and a proportion of arachidonic acid with respect to total fatty acids contained as constituents of total phosphatidylserine is 20 percent by weight or greater.

2. The phospholipids as set forth in claim 1,
    wherein the LCPUFA-PL includes phosphatidylcholine that at least includes dihomo-γ-linolenic acid as LCPUFA, and
    wherein a proportion of dihomo-γ-linolenic acid with respect to total fatty acids contained as constituents of total phosphatidylcholine is 3 percent by weight or greater.

3. The phospholipids as set forth in claim 1,
    wherein the LCPUFA-PL includes phosphatidylserine that at least includes dihomo-γ-linolenic acid as LCPUFA, and
    wherein a proportion of dihomo-γ-linolenic acid with respect to total fatty acids contained as constituents of total phosphatidylserine is 1 percent by weight or greater.

4. A lipid composition containing phospholipids of claim 1.

5. The lipid composition as set forth in claim 4, which is used as a nutritional composition.

6. The lipid composition as set forth in claim 4, which is processed into a capsule or tablet.

7. Food containing the lipid composition of claim 4.

8. The food as set forth in claim 7, which is an oil-in-water dispersion liquid in the form of a liposome formed by the phospholipids.

9. The food as set forth in claim 7, which is a nutriment.

* * * * *